(12) United States Patent
Vesely

(10) Patent No.: US 6,943,147 B2
(45) Date of Patent: Sep. 13, 2005

(54) CANCER TREATMENT USING PROANP PEPTIDES

(75) Inventor: David L. Vesely, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/708,688

(22) Filed: Mar. 18, 2004

(65) Prior Publication Data

US 2004/0229784 A1 Nov. 18, 2004

Related U.S. Application Data

(60) Provisional application No. 60/320,018, filed on Mar. 19, 2003.

(51) Int. Cl.[7] .......................... A61K 38/00; C07K 5/00; C07K 7/00
(52) U.S. Cl. .......................... 514/12; 514/13; 530/324; 530/326
(58) Field of Search ................................ 514/2–12, 13; 530/324, 326

(56) References Cited

PUBLICATIONS

Wigle, D.A., Campling, B.G., Sarda, I.R., Shin, S.H., Watson, J.D., Frater, Y., Flynn, T.G., and Pang, S.C. ANP Secretion from small cell lung cancer lines: a potential model of ANP release (1995) Am J Physiol. 268(5 Pt 2): H1869–74.*

David L. Vesely, Atrial Natriuretic Peptides in Pathophysiological Diseases, Cardiovascular Research, 2001, 51(2001) p. 647–658.

Vesely, D.L. et al., Novel Therapeutic Approach for Cancer Using Four Cardiovascular Hormones, European Journal of Clinical Investigation, 2004, 34.

* cited by examiner

*Primary Examiner*—Karen Cochrane Carlson
*Assistant Examiner*—Marsha Tsay
(74) *Attorney, Agent, or Firm*—Smith & Hopen, P.A.

(57) ABSTRACT

The present invention includes a method of utilizing four peptide hormones to inhibit theasein the number of human pancreatic adenocarcinoma cells (i.e., the type of cancer with the highest mortality, with patients only surviving four months) was observed responsive to treatment. The application of the invention would be to utilize one or more of these peptide hormones alone and/or in combination to treat cancer. The ability of these peptide hormones to decrease the number of adenocarcinoma cells has implications for adenocarcinomas at other sites in the body with the majority of cancers of the breast, colon and prostate also being adenocarcinomas. Adenocarcinomas also occur in the lung and other tissues. Treatment of a wide variety of cancers in addition to adenocarcinomas is anticipated by the present invention.

10 Claims, 7 Drawing Sheets

Vessel dilator (■), long acting natriuretic peptide (○, LANP), kaliuretic peptide (▼), and atrial natriuretic peptide (ANP, ▽) compared to control (●) adenocarcinoma cells.

FIG. 6

Four peptide hormones effects on mediators of apoptosis.

|  |  | Control | LANP | Vessel Dilator | Kaliuretic Peptide | ANP |
|---|---|---|---|---|---|---|
| Caspases | 9 | + | + | + | + | + |
|  | 3 | + | + | + | + | + |
|  | 7 | + | + | + | + | + |
| Cleaved Caspases | 9 | + | + | + | + | + |
|  | 3 | + | + | + | + | + |
|  | 7 | + | + | + | + | + |
| PARP |  | + | + | + | + | + |
| Cleaved PARP |  | + | + | + | + | + |

LANP = long acting natriuretic peptide, ANP = atrial natriuretic peptide, PARP = poly (ADP-ribose) polymerase Graded 0 to ++++, with ++++ being the strongest staining observed. This table illustrates that basal caspase activity was low (+) and not significantly enhanced in the pancreatic adenocarcinoma cells by any of the peptide hormones at their 1µM concentrations when examined by repeated analysis of variance.

Step 1

Step 2

Step 3

Step 4

CANCER TREATMENT USING PROANP PEPTIDES

CROSS-REFERENCE TO RELATED DISCLOSURES

This application claims priority of a provisional application of the same title, filed Mar. 19, 2003 by the present inventor and bearing application Ser. No. 60/320,018.

BACKGROUND OF INVENTION

1. Field of the Invention

The invention relates to the field of treating cancer.

2. Background

In 1628, William Harvey first demonstrated the heart was a pump, pushing blood to the lungs for oxygenation, and then through the peripheral vascular system to bring oxygen and nutrients to every cell in the body. It was another 350 years before the heart was established as an endocrine gland. This discovery was stimulated by the experiments of deBold et al. who infused extracts of atria of rat hearts into other rats which resulted in a 10-fold increase in water excretion and 30-fold increase in sodium excretion. It is now known that there are a number of peptide hormones synthesized within the heart and this family is called atrial natriuretic peptides (ANPs). These peptides were so named because they are synthesized mainly in the atria of the heart and one of their main biologic functions is to enhance sodium excretion (i.e., natriuresis). Atrial natriuretic peptides are synthesized by three different genes and then stored as three different prohormones (i.e., 126 amino acid [a.a.] atrial natriuretic peptide (ANP), 108 a.a. brain natriuretic peptide (BNP), and 126 a.a. C-natriuretic peptide (CNP) prohormones). Atrial natriuretic peptide, further, is part of a hormonal system in which one gene synthesizes four peptide hormones (FIG. 1). The ANP gene synthesizes a 151 preprohormone which is processed within the endoplasmic reticulum to form a 126 a.a. prohormone (i.e., the storage form of the following peptide hormones) after removal of a 25 a.a. signal peptide from its N-terminal end (FIG. 1).

These four peptide hormones within the 126 a.a. ANP prohormone consist of:

(1) the first 30 amino acids from the N-terminal end of the prohormone (i.e., proANP 1–30; long acting natriuretic peptide, LANP);

(2) a.a. 31–67 (i.e., proANP 31–67; vessel dilator);

(3) a.a. 79–98 (proANP 79–98; kaliuretic peptide); and (4) a.a. 99–126 (ANP) of this prohormone (FIG. 1).

Each of these four peptide hormones circulate within the blood stream with LANP and vessel dilator's concentrations in plasma being 15- to 20-fold higher than ANP. Each of these peptide hormones have biologic effects, e.g., blood pressure lowering, natriuretic and/or diuretic effects in both animals and humans.

SUMMARY OF INVENTION

The present invention comprises a method of inhibiting the growth of cancer cells comprising the step of contacting at least one target cell with an effective amount of a peptide hormone derived from the ANP prohormone. The peptide hormone administered is derived from the ANP prohormone and is selected from the group consisting of atrial natriuretic peptide, long acting natriuretic peptide, vessel dilator, and kiliuretic peptide. In one embodiment, the target cell is chosen from the group consisting of adenocarcinomas, small cell carcinomas and squamous cell carcinoma, and the peptide hormone is administered in vivo.

In another embodiment, the invention includes a method of inhibiting the growth of cancer cells comprising the step of co-administering, to at least one target cell, an effective amount of a combination of peptide hormones derived from the ANP prohormone. Again, the combination of peptide hormones is derived from the ANP prohormone is selected from the group consisting of atrial natriuretic peptide, long acting natriuretic peptide, vessel dilator, and kiliuretic peptide. In another embodiment the target cell is chosen from the group consisting of adenocarcinomas, small cell carcinomas and squamous cell carcinoma, and the combination of peptide hormones is administered in vivo.

Human pancreatic adenocarcinoma cells where chosen because this cancer has the lowest five-year survival rate of all common cancers. The five-year survival rate with adenocarcinoma of the pancreas is 1%, and the median survival is 4.1 months. Surgery and chemotherapy extend survival by a few months but the above five-year survival rate includes treatment with surgery and chemotherapy. Another important reason for choosing pancreatic adenocarcinoma cells to study is that there is a strong association with cigarette (i.e., tobacco) smoking causing pancreatic adenocarcinomas. The importance of the present discovery is that vessel dilator, LANP and kaliuretic peptide have never been investigated to determine whether they inhibit cancer cells from proliferating and/or kill the cancer cells themselves. This discovery is particularly meaningful in that the cancer chosen has the highest mortality of all cancers and all four of the peptide hormones tested inhibited the cancer cells from proliferating and significantly ($P<0.001$) decreased their number. One of the peptide hormones (i.e., vessel dilator) decreased the number of adenocarcinoma cells 70%, i.e., there were 70% less cancer cells present when exposed to vessel dilator and 65% less within 24 hours. This decrease in adenocarcinoma cells is very significant when compared to the anti-cancer agent 5-fluorouracil (5-FU) that was the mainstay of treatment of pancreatic adenocarcinomas for 45 years. 5-FU inhibits pancreatic adenocarcinoma cells growth in culture by 16%. There is now evidence that vessel dilator can inhibit the growth of human pancreatic adenocarcinoma in vivo i.e., in whole animals as will be detailed below.

BRIEF DESCRIPTION OF DRAWINGS

FIG. 6 shows the effects within the adenocarcinoma cells on several of the caspases, a family of cysteine asparatic proteases which are central regulators of apoptosis.

DETAILED DESCRIPTION

In the following detailed description of the preferred embodiments, reference is made to the accompanying drawings, which form part hereof, and within which are shown by way of illustration specific embodiments by which the invention may be practiced. It is to be understood that other embodiments may be utilized and structural changes may be made without departing from the scope of the invention.

Figure 1:
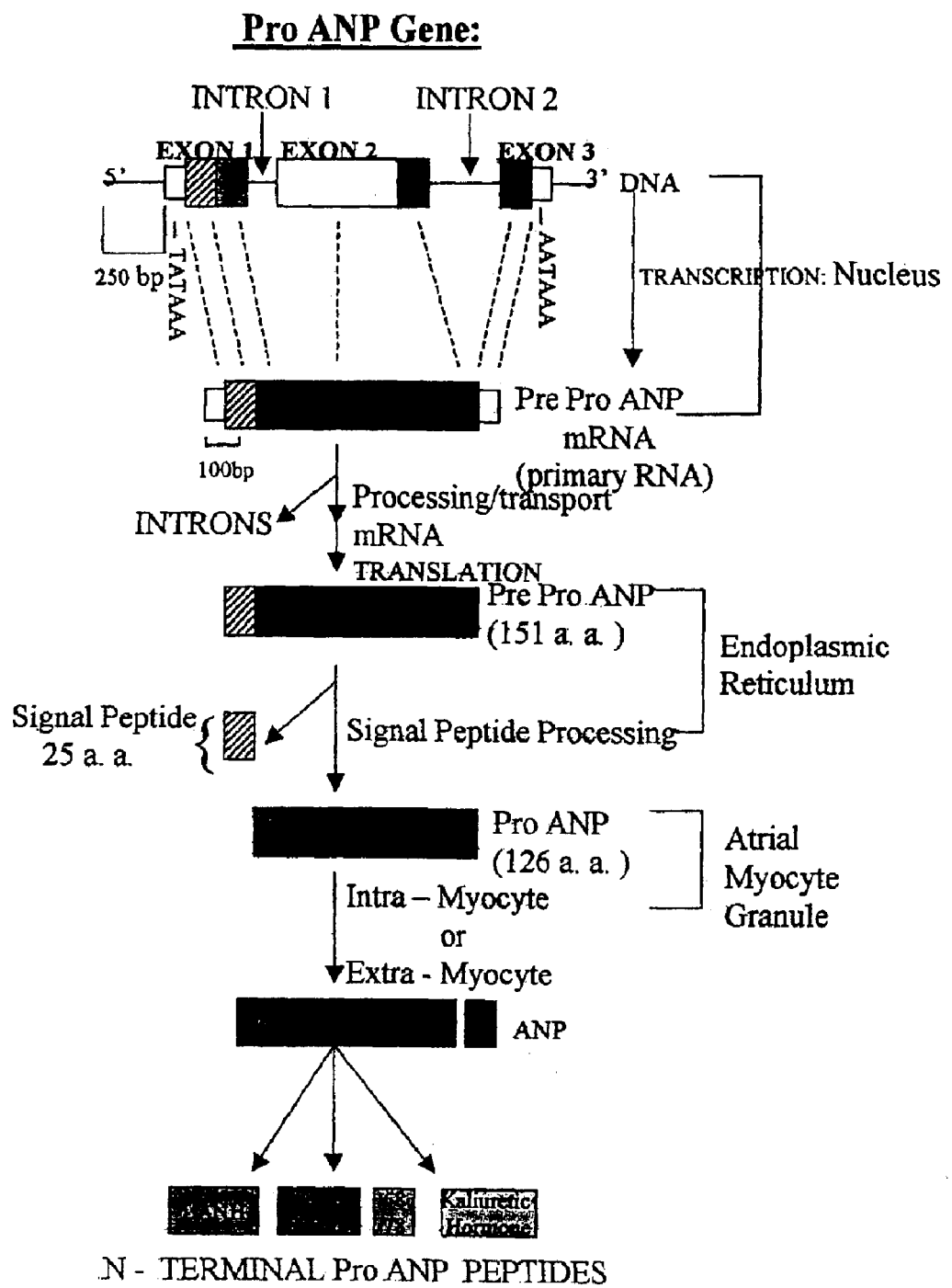
FIG. 1 shows the structure of the atrial natriuretic peptide prohormone (proANP) gene. Four peptide hormones, (e.g., atrial natriuretic peptide (ANP), long acting natriuretic peptide (LANP), vessel dilator, and kaliuretic peptide are synthesized by this gene. Each of these peptide hormones have biologic effects e.g., natriuresis and diuresis.

The atrial natriuretic peptide prohormone gene synthesizes four peptide hormones which lower blood pressure and enhance salt and water metabolism. (see Vesely, David L., Atrial natriuretic peptide prohormone gene expression: Hormones and diseases that upregulate its expression. IUBMB Life 53:153–159, 2002 which is incorporated herein by reference. Dr. deBold in Canada discovered atrial natriuretic peptide (ANP) while the three other peptide hormones were discovered by the present inventor. These three peptides consist of amino acids (a.a.) 1–30, 31–67, and 79–98 of the 126 a.a. ANP prohormone and have been tentatively named long acting natriuretic peptide, vessel dilator, and kaliuretic peptide, respectively (FIG. 1).

The heart synthesizes a number of peptide hormones whose main known functions are to lower blood pressure and enhance sodium and water excretion. One of these peptide hormones, i.e., atrial natriuretic peptide (ANP), has growth regulatory properties in blood vessels where it inhibits smooth muscle cell proliferation (hyperplasia) as well as smooth muscle cell growth (hypertrophy). ANP has growth-regulatory properties in a variety of other tissues including brain, bone, myocytes, red blood cell precursors, and endothelial cells. In the kidney, ANP causes antimitogenic and antiproliferative effects in glomerular mesangial cells.

The known growth regulatory properties of ANP formed the rationale to investigate whether ANP and the three other peptide hormones (FIG. 1) that are synthesized by the same gene (and have similar biological effects as ANP) can inhibit the growth and/or decrease the number of cancer cells. The other three cardiac hormones in this investigation have never been evaluated for any possible growth regulatory properties in either smooth muscle cells (like ANP), or in cancer cells even though their other biologic effects are similar to ANP. The theory upon which the present invention was founded is that one or more of these peptide hormones synthesized within the heart can inhibit the growth of cancer cells. When each of these cardiac hormones were found to significantly decrease the number of adenocarcinoma cells, a secondary theory was formulated. The secondary theory is that the mechanism of the decrease in number of cancer cells and the ability of these peptides to inhibit further proliferation of these cancer cells for three days by these peptide hormones is due to an inhibition of DNA synthesis and/or due to their enhancing programmed cell death, e.g. apoptosis.

Test Preparation of Pancreatic Adenocarcinoma Cells

The pancreatic adenocarcinoma cell line, ATCC number CRL-2119, was derived in 1985 from a nude mouse xenograft of a primary tumor removed from the head of the pancreas. It is a moderate to well-differentiated pancreatic adenocarcinoma of ductal origin. These pancreatic adenocarcinoma cells are stimulated to proliferate in culture by insulin, insulin-like growth factor I (IGF-I), epidermal growth factor (EGF), and transforming growth factor alpha (TGF alpha). These adenocarcinoma cells contain significant concentrations of tumor-associated antigens CEA, CA 125, and CA 19-9. In culture, these adenocarcinoma cells form monolayers of morphologically heterogeneous polar epithelial cells. These cells are tumorgenic in that they form tumors in athymic nude mice at the site of inoculation that are histologically similar to the tumor of origin.

Culture of Pancreatic Adenocarcinoma Cells

Propagation of these cells was in Dulbecco's modified Eagle's plus Ham's F12-A 1:1 mixture of Dulbecco's modified Eagle's medium and Ham's F12 medium containing 1.2 g/L of sodium bicarbonate (Sigma Chemical Co., St. Louis, Mo.) supplemented with 15 mM HEPES and fetal bovine serum, 10%, at a temperature of 37° C. as recommended by the ATCC.

These pancreatic adenocarcinoma cells were subcultured (passaged) by removing spent (i.e., old) medium by aspiration, and then adding calcium and magnesium free Hank's Balanced Salt Solution with 0.25% trypsin and 0.03% ethylenediaminetetracetic acid (EDTA). The culture was allowed to sit at room temperature for 2 to 5 minutes. Fresh medium was added to the adenocarcinoma cells which were dispensed into new flasks, with subculture every 6 to 8 days. The growth medium was changed every three days.

After these adenocarcinoma cells were subcultured for 24 hours, they were then seeded to coverslips and transferred to 24 microwell plates (NUCOLON, Roskilde Denmark), with 1 ml Dulbeco Modified Eagle's (DME)/Falcon-12 nutrient culture media (Sigma Chemical Co.) with 10% fetal bovine serum (Atlanta Biologicals, Norcross, Ga.). After 24 hours, wells were washed twice with Dulbecco's Modified Eagle's/ Ham's F12 with 0.1% bovine serum albumin (Sigma-Aldrich, St. Louis, Mo.) and allowed to incubate in this serum free medium for an additional 24 hour period of serum deprivation. Serum-free media was utilized to remove all variables (EGF, etc.) present in serum in order that interpretation of any data obtained would be straightforward. After 24 hours of serum deprivation, media volume was reduced to 250 µL per well with or without the respective peptide hormones at their 1 µM concentrations (1% of this volume). The adenocarcinoma cells were then incubated for various periods of time (24, 48, 72, and 96 hours). At the end of the above time periods, hematoxylin was added for 5 minutes to make the cells more visible for counting, and then they were washed for 5 minutes. The coverslips were then placed face down on microscope slides with the addition of 6 µl of histologic grade phosphate buffered saline (PBS)/I-glycine that had been filtered immediately before use with a 0.22 μm polyethersulfone, nonpyrogenic, sterile, low protein binding membrane (Corning 43117, Corning Inc., Corning, N.Y.). The number of adenocarcinoma cells were then counted with a cell counter evaluating ten fields of the microscope slide at 40× along the X-axis with an Olympus BH-2 microscope (Atlanta, Ga.). This evaluation was repeated on six separate occasions with the number of adenocarcinoma cells reflecting 60 observations for each group, i.e., 60 observations for controls and 60 observations for each of the four groups with respective peptide hormones. The only variable in this investigation was whether one of the four peptide hormones was added to the pancreatic adenocarcinoma cells. Otherwise all the adenocarcinoma cells were treated the same, i.e., with same culture medium, time of incubation, and processing of cells for the various investigations. The peptide hormones used in this investigation were from Peninsula Laboratories, Belmont, Calif.

Determination of DNA Synthesis and Cell Proliferation

To investigate whether these peptide hormones were inhibiting DNA synthesis and cell proliferation bromodeoxyuridine (BrdU) incorporation into the adenocarcinoma cells was utilized. BrdU was from BD Bioscience, San Jose, Calif. DNA synthesis and doubling of the genome take place during the synthetic or S phase. BrdU is a thymidine analog incorporated into nuclear DNA during the S phase of the cell cycle. Immunohistochemical methods use BrdU also as a marker of cell proliferation in cancer biology studies. After 24 hours in culture with 1 μM of LANP, vessel dilator, kaliuretic peptide, or ANP, respectively, or with no peptide hormone (i.e., control), BrdU in a final concentration of 10 μM in the cell culture medium was added for 45 minutes—which is time in which the cells are in the logarithmic phase of cell proliferation. For immunohistochemistry, a BrdU in situ detection kit from Becton Dickinson Immunocytochemistry Systems, San Jose, Calif., was utilized.

After the 45 minutes with BrdU, the adenocarcinoma cells were washed three times in phosphate buffered saline (PBS), five minutes each. This was followed by placing the cells in a −80° C. freezer for five minutes and then 100% methanol was added at 5° C. in order for the cells to become permeable enabling the anti-BrdU antibody to reach the nucleus of the cell. The cells were then washed again in PBS before 100 μl of biotinylated anti-BrdU antibody was added. The coverslips were then incubated in a humidified chamber for one hour. After this incubation, the slides were rinsed in PBS, two minutes each. Then streptavidin-horseradish peroxidase (HRP) was added to each coverslip. The cells were then incubated for 30 minutes. Streptavidin-HRP binds to biotinylated anti-BrdU and HRP is used with addition of diaminobenzidine (DAB) substrate system to visualize BrdU incorporation into the adenocarcinoma cells. After the 30 minute incubation with streptavidin-HRP, the coverslips were rinsed in PBS, two minutes each time, before adding the DAB substrate solution, which contains DAB chromagen and DAB buffer, for five minutes. The coverslips were then rinsed in water, two minutes each time before counterstaining the slides with hematoxylin for 60 seconds followed by a thorough rinsing in water for five minutes. The incorporation of the BrdU stain into the nucleus was then counted using a Nikon Inverted Diaphot-TMD Microscope (Tokyo, Japan). The number of stained nuclei was compared in the four peptide hormone groups to the positive control group. The negative control for these studies was provided by Becton Dickinson Immunocytochemistry Systems.

To investigate DNA synthesis, BrdU incorporation by immunocytochemistry has been demonstrated to be equally good as $^3$H-thymidine incorporation. BrdU has an advantage over $^3$H-thymidine incorporation in that it takes less time and provides high resolution.

To determine mechanism of how these peptides inhibit DNA synthesis in cancer cells the following investigation was done.

Cyclic GMP and Prostaglandin $E_2$ Effects on DNA Synthesis (Mechanism of Action Studies)

Cyclic GMP and prostaglandin $E_2$ are the two known mediators of all of the previously described biologic effects of these four peptide hormones. All four of these peptide hormones-induced vasodilation of vasculature is mediated by increased cyclic GMP concentrations via enhancing guanylate cyclase activity. The natriuretic effects of long acting natriuretic peptide, kaliuretic peptide and vessel dilator have different mechanism(s) of action from ANP in that they inhibit renal $Na^+$—$K^+$-ATPase secondary to their ability to enhance the synthesis of prostaglandin $E_2$ which ANP does not do. ANPs effects in the kidney are thought to be mediated by cyclic GMP. Each of these peptide hormones increase cyclic GMP while simultaneously dilating vasculature. 8 bromo-cyclic GMP reproduces these vasodilatory effects. For the present investigation of the mechanism of these peptide hormones' ability to inhibit DNA synthesis in cancer cells, 8-bromoguanosine 3',5'-cyclic monophosphate (i.e., 8-bromo cyclic GMP, Sigma-Aldrich Co., St. Louis, Mo.) was utilized. 8-bromo cyclic GMP is a cell-permeable analog of cyclic GMP. 8-bromo cyclic GMP effects on DNA synthesis were investigated in dose-response curves with cyclic GMP concentrations ranging from 100 pM to 5 mM.

Prostaglandin $E_2$, i.e., (5Z, 11α, 13E, 15S)-11, 15-dihydro-9-oxo-prosta-5, 13-dien-I-oic acid was purchased from Sigma-Aldrich, St. Louis, Mo. Prostaglandin $E_2$ was utilized in concentrations ranging from 10 pg/ml to 1 mg/ml to obtain its dose-response effects on DNA synthesis in adenocarcinoma cells. The pancreatic adenocarcinoma cells were exposed to the varying concentrations of 8-bromo cyclic GMP and prostaglandin $E_2$ for 24 hours before determining DNA synthesis by the above method.

Evaluation of Apoptosis (Programmed Cell Death)

To determine if enhancing programmed or "suicidal" cell death (e.g. apoptosis) was involved in the mechanism of action of these peptide hormones' ability to decrease the number of adenocarcinoma cells these four peptides' effects were examined on several of the caspases (a family of cysteine asparatic acid proteases which are central regulators of apoptosis). Caspase 9, a key initiator caspase, when activated, produces a cleaved caspase-9, which, in turn, activates procaspases-3 and 7 to produced cleaved capases 3 and 7 which cleave cytoskeletal and nuclear proteins like poly (ADP-ribose) polymerase (PARP) which induces apoptosis. Each of these caspases and PARP were evaluated in the above adenocarcinoma cells utilizing an apoptosis immunohistochemistry kit from Cell Signaling Technology (Beverly, Mass.) after incubation of the above cancer cells with and without 1 μM of the above cardiac hormones for 24 hours. This apoptosis evaluation used primary polyclonal antibodies produced by Cell Signaling Technology via immunizing rabbits with synthetic peptides (KLH coupled) corresponding to residues surrounding the cleavage sites of caspase-3, -7, -9, and PARP. All of these antibodies are purified by protein A and peptide affinity chromatography. Caspase-3 antibody detects endogenous levels of full-length caspase-3 which is 35 kilo Dalton, (kD, approximately 35000 molecular weight) and a large fragment of caspase-3 resulting from cleavage (17 kD). Cleaved caspase-3 (Asp 175) antibody detects endogenous levels of the large fragment (17/19 kD) of activated caspase-3 resulting from cleavage adjacent to Asp 175. This antibody does not recognize full-length caspase-3 or other cleaved capases. Caspase-7 antibody detects endogenous levels of both full-length capase-7 (35 kD) and a large fragment of cleaved caspase-7 following cleavage at Asp 198 (20 kD). This antibody does not recognize other caspases. Cleaved caspase-7 (Asp 198) antibody detects endogenous levels of the large fragment of capase-7 following cleavage at Asp 198. This antibody does not cross react with full-length caspase-7 or with other caspases. Caspase-9 antibody detects endogenous levels of full-length caspase-9 (47 kD) and a large 17 kD subunit of caspase-9. This antibody does not recognize other caspases. Cleaved caspase-9 (Asp 330) antibody detects endogenous levels of the large fragment (37 kD with prodomain/17 kD) of caspase-9 following cleavage at Asp 330. This antibody does not recognize uncleaved procaspase-9.

Nuclear poly (ADP-ribose) polymerase (PARP) antibody detects endogenous amounts of full-length PARP (116 kD), as well as a large fragment (89 kD) and small fragment (24 kD) of PARP. Cleaved PARP (Asp 214) antibody detects endogenous levels of the large fragment (89 kD) of PARP produced by caspase cleavage. This antibody does not react with full-length PARP.

These caspase investigations were performed as follows: The adenocarcinoma cells after 24 hours with and without 1 $\mu$M of the respective peptides were treated with freshly made 1% $H_2O_2$ (0.1 ml of 30% $H_2O_2$ in 3 ml of Tris buffered saline [TBS] pH 7.5), for 30 minutes. Nonspecific binding sites for the respective caspases were blocked by 3% bovine serum albumin (BSA) in TBS for one hour. These cells were then incubated with the respective primary caspase antibody diluted in 3% BSA/TBS overnight at 4° C. The next day these cells on coverslips were washed in TBS at room temperature before incubating for 1 hour with biotinylated anti-rabbit secondary antibody. These cells were then washed in TBS for ten minutes each before adding freshly prepared avidin-biotin-peroxidase complex solution (Vectastain ABC kit, Vector Laboratories, Burlingame, Calif.) for one hour at room temperature. The cells were then washed in TBS, ten minutes each, followed by incubation in diaminobenzidine (DAB) solution until the staining was optimal as determined by light microscopic exam. The cells were finally washed in TBS for five minutes each before mounting the coverslips on gelatin coated slides for drying at room temperature. The slides were then evaluated with a Nikon Inverted Diaphot-TMD Mocroscope (Tokyo, Japan).

Whole Animal Model for In Vivo Anticancer Investigations

The animals used in the whole animal studies were NCr athymic nude mice. The NCr athymic outbred stock is the standard athymic model for National Cancer Institute (NCI) studies as well as many pharmaceutical and institutional oncology screening programs. The nude gene in homozygous (nu/nu) mice causes the lack of fur and an abnormal thymus. The deficiency in T cell function allows athymic mice to accept and grow xenografts as well as allografts of normal and malignant tissues. Heterozygous (nu/+) animals carry the recessive nude gene on one chromosome only and therefore have a normal thymus triggered immune system. NCr-nu breeder stock was obtained from the NCI in 1993 after several years of random breeding. It was hysterectomy derived to achieve germfree status prior to its introduction into IBU colonies. This outbred stock has both BALB/c inbred and NIH(S) outbred stock in its genetic background. The homozygotes (nu/nu) used for the proposed investigations are albino animals with the model number of NCRNU-M from Tacoma Farms also being called Tac:Cr: (NCr)-Foxn1$^{nu}$: Six week old nude mice were utilized for these studies as they weight approximately 20 grams at this time period and the subcutaneous pumps used to infuse the respective four atrial natriuretic peptides were designed for 20 gram and larger mice. These mice accept malignant tissues. After one week of accliminization to their new surroundings, the mice have 1×10$^6$ of the adenocarcinoma cells placed under the skin on their backs. Approximately nine days (and up to 14 days) later these adenocarcinoma cells grow into a well defined tumor of 1 mm×1 mm (volume=0.5 mm$^3$). Tumor volume was calculated by the formula V (volume)=a×b$^2$/2 where "a" is the largest superficial diameter and b is the smallest superficial diameter. These mice were palpitated at the site of injection daily to determine the latency of the respective tumor formation(s). Tumor growth was followed by Vernier caliper measurements every day. When the tumors first became palpable their volume was recorded and then an osmotic pump (Alzet Model 1002) containing either 0.9% saline (control infusion) or one of the respective peptide hormones in 0.9% saline was placed subcutaneously between the shoulder blades under anesthesia (pentobarbital 40 mg/kg body wt intraperitoneally). The osmotic pump pumps these peptides continuously for 14 days. (The Alzet Model 1002 pump for mice delivers all of its contents (100 $\mu$l) over 14 days at a rate of 0.25 $\mu$l/hr and then stops pumping.)

Decrease in Number of Adenocarcinoma Cells by Four Cardiac Peptide Hormones

Figure 2:
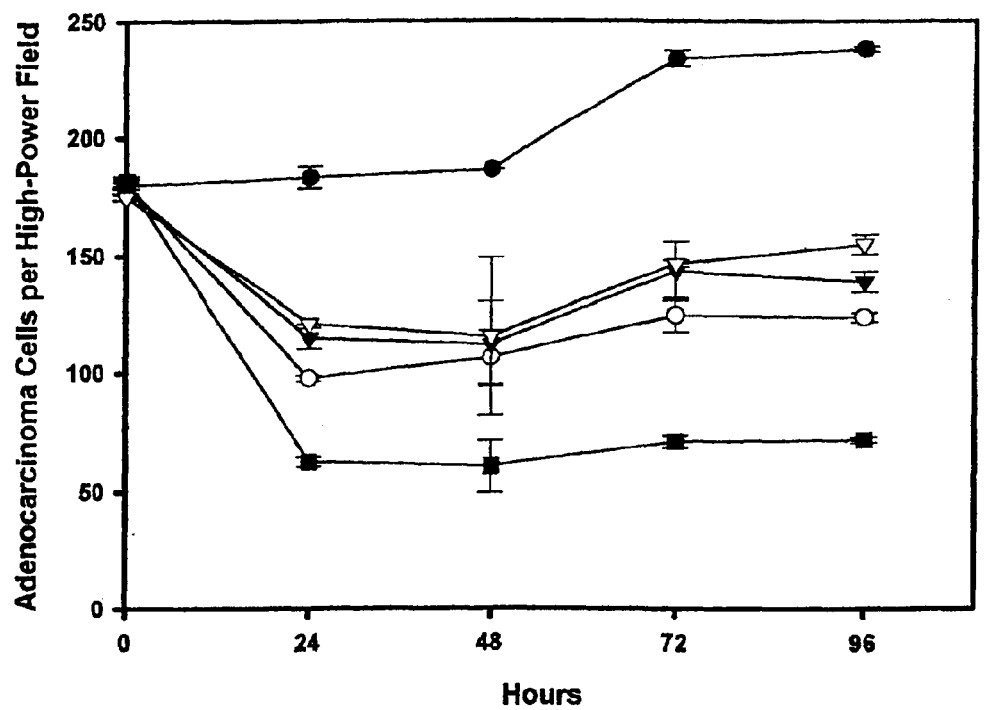
FIG. 2 illustrates time course of inhibition of pancreatic adenocarcinoma cell growth by vessel dilator, long acting natriuretic peptide (LANP), kaliuretic peptide, and atrial natriuretic peptide (ANP) compared to control adenocarcinoma cells.

FIG. 2 illustrates time course of inhibition of pancreatic adenocarcinoma cell growth by vessel dilator, long acting natriuretic peptide (LANP), kaliuretic peptide, and atrial natriuretic peptide compared to control adenocarcinoma cells. The decrease in cell number by ANP and kaliuretic peptide was significant at P<0.05 while the decrease secondary to LANP and vessel dilator were significant at P<0.01 and at P<0.001, respectively, when evaluated by repeated analysis of variance (ANOVA). The decrease in number of adenocarcinoma cells secondary to vessel dilator was significantly greater (P<0.05) than the decrease secondary to ANP and kaliuretic peptide while the decrease in adenocarcinoma cells secondary to LANP was not significantly different than the decrease caused by vessel dilator when evaluated by ANOVA.

The number of adenocarcinoma cells after 24 hours without the addition of any of the peptide hormones averaged 183.4+/−8 cells per high powered field when ten fields of the microscope slide were evaluated at 40× along the x-axis with an Olympus BH-2 Microscope (Atlanta, Ga.). This evaluation was repeated on six separate occasions with the above number reflecting sixty observations of the number of adenocarcinoma cells growing in culture with and without the cardiac hormones (FIG. 2). The addition of 1 $\mu$M of long acting natriuretic peptide (LANP) for 24 hours decreased the number of adenocarcinoma cells to 97.7+/−3 i.e., a 47% decrease (P<0.01) in the number of adenocarcinoma cells with the LANP (FIG. 2). Vessel dilator at 1 $\mu$M for 24 hours had an even more dramatic decrease (65%, P<0.001) in the number of these adenocarcinoma cells (FIG. 2). Vessel dilator decreased the number of cancer cells by 65%, i.e., from 183.4+/−8 cells to 63.8+/−4 adenocarcinoma cells. Kaliuretic peptide at 1 $\mu$M for 24 hours decreased the number of adenocarcinoma cells 37% (P<0.05) i.e., to 115+/−3 adenocarcinoma cells (FIG. 2).

The number of adenocarcinoma cells in culture decreased 34% (P<0.05) when exposed to atrial natriuretic peptide (1 $\mu$M) for 24 hours (FIG. 2). Thus, with respect to their ability to decrease the number of adenocarcinoma cells when these cells were exposed to identical concentrations of these four peptide hormones for 24 hours, vessel dilator>LANP>kaliuretic peptide>ANP. Kaliuretic peptide and ANP decreased the number of pancreatic adenocarcinoma cells growing by approximately ⅓ but LANP decreased the growth of adenocarcinoma cells nearly in half while with the addition of vessel dilator there were ⅔ less cancer cells at 24 hours than in the untreated group. The decrease in number of adenocarcinoma cells secondary to vessel dilator was significantly greater (P<0.05) at each time point than the decrease in the number of these cells by ANP and kaliuretic peptide. Comparing the abilities of vessel dilator and LANP to decrease in the number of adenocarcinoma cells, the difference between these two peptides did not reach statistical significance. When the number of cells was examined immediately after the incubation of the respective peptide hormones within the cells, there was not any decrease in the number of cancer cells. In the wells with decreased number of cells secondary to the cardiac hormones, there was evidence of cellular debrie.

Decreased Cellular Proliferation After Initial Decrease in Adenocarcinoma Cell Number When these adenocarcinoma cells were exposed for longer periods of time e.g., 48, 72, and 96 hours to vessel dilator, LANP, kaliuretic peptide, and ANP each at 1 $\mu$M, there was a nearly complete inhibition of the proliferation of the adenocarcinoma cells after the decrease in number of cancer cells at 24 hours (FIG. 2). Thus, when exposed to vessel dilator, LANP, kaliuretic peptide and ANP for 48 hours the number of cancer cells compared to controls was 68% (P<0.001), 43%, 40% and 33% (P<0.05 for these three peptides) respectively. At both 72 hours and 96 hours, vessel dilator decreased in number of adenocarcinoma cells by 70% (P<0.001) (FIG. 2). The addition of LANP (1 $\mu$M) for 72 and 96 hours reduced the number of adenocarcinoma cells 47% and 48% (P<0.001), respectively, compared to untreated adenocarcinoma cells. At 72 and 96 hours, kaliuretic peptide decreased the number of cancer cells compared to control cells by 39% and 42% (P<0.05 for both) (FIG. 2). ANP decreased the number of adenocarcinoma cells growing at 72 and 96 hours by 37% and 35% (P<0.05 for both), respectively, compared to the number of adenocarcinoma cells growing at these same time periods without the addition of any peptide hormone (FIG. 2). Thus, proliferation was inhibited by these peptide hormones for three days after the initial decrease in cell number at 24 hrs. There was not any increase in proliferation of any of the cancer cells when exposed to these four peptides for 1, 2, and 3 days after the initial decrease in the number of adenocarcinoma cells within the first 24 hours. When the growth of pancreatic adenocarcinoma cells was evaluated at 96 hours, vessel dilator continued to have the strongest growth inhibitory properties, with a 70% reduction in the number of adenocarcinoma cells. LANP continued to decrease the number of the adenocarcinoma cells in half (i.e., 48%) at 96 hours while kaliuretic peptide caused a decreased number of cancer cells to be present at 96 hours (i.e., 42% decreased number) compared to its inhibition on the growth of these cancer cells at 24 hours (i.e., 34% decrease). The cancer growth inhibitory properties of ANP at 96 hours was similar to its effects at 24 hours (i.e., 35% vs. 34% decreased cancer cells compared to untreated cancer cells).

Inhibition of DNA Synthesis by Four Peptide Hormones

Figure 3:
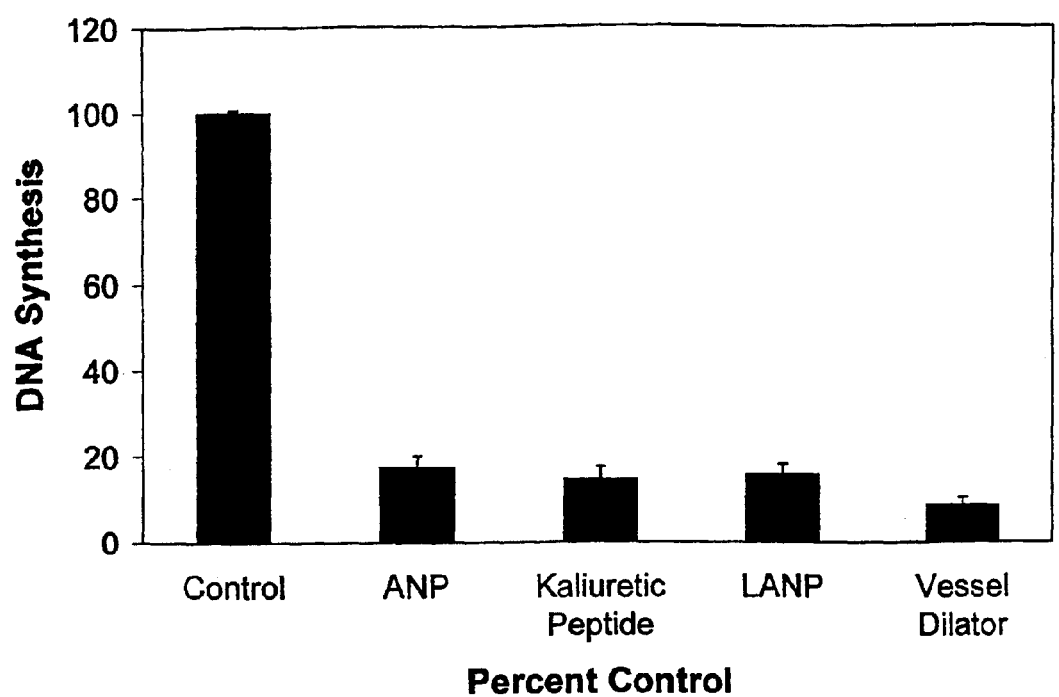
FIG. 3 shows inhibition of DNA synthesis by vessel dilator, long acting natriuretic peptide (LANP), kaliuretic peptide, and atrial natriuretic peptide (ANP) in pancreatic adenocarcinoma cells. This inhibition of DNA synthesis is illustrated as the percent of DNA synthesis occurring in these cancer cells with the respective peptide hormones, each at 1 $\mu$M, versus the amount of DNA synthesis in the adenocarcinoma cells without the addition of any of these peptide hormones. The amount of inhibition of DNA synthesis by each of these peptide hormones was significant at $P<0.001$ when evaluated by repeated analysis of variance.

To help determine the mechanism of the adenocarcinoma cells' decrease in number and decreased cellular proliferation by these four peptide hormones, it needed to be determined whether their effects were due to an inhibition of DNA synthesis and/or due to enhancing programmed cell death, e.g. apoptosis. Vessel dilator, LANP, kaliuretic peptide and ANP each at their 1 $\mu$M concentrations inhibited DNA synthesis (i.e., cell proliferation) when incubated with adenocarcinoma cells for 24 hours by 91%, 84%, 86% and 83%, respectively (P<0.001 for each) (FIG. 3).

Cyclic GMP Inhibits DNA Synthesis in Adenocarcinoma Cells

Figure 4:
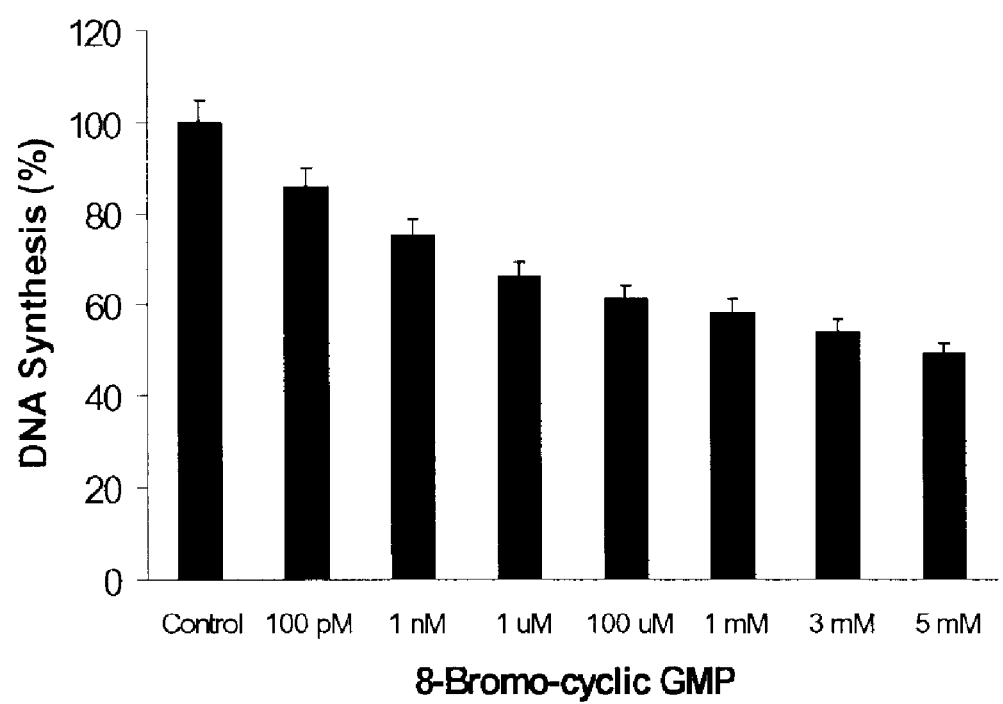
FIG. 4 is a graph showing 8-bromo cyclic GMP (intracellular mediator of the peptides' effects) inhibits DNA synthesis in pancreatic adenocarcinoma cells. 8-bromo cyclic GMP at its 5 mM, 3 mM, 1 mM, 100 M, 1 µM and 1 nM concentrations, respectively, decreased DNA synthesis 51% ($P<0.01$) 46%, 42%, 39%, 34%, and 25% (all $P<0.05$) when evaluated by repeated analysis of variance. 8-bromo cyclic GMP effects at its 100 pM concentration were not significant when evaluated by repeated analysis of variance.

To help define the mechanism(s) for these peptide hormone's ability to decrease DNA synthesis, one of the known mediators of these peptides biologic effects, i.e., cyclic GMP was investigated to determine if it could inhibit DNA synthesis in these same pancreatic adenocarcinoma cells. 8-bromo cyclic GMP decreased DNA synthesis in pancreatic adenocarcinoma cells by 51% (P<0.01) at its 5 mM concentration (FIG. 4). Dose response curves revealed that 8-bromo cyclic GMP decreased DNA synthesis in these cancer cells 46%, 42%, 39%, and 34% (all P<0.05) at its 3 mM, 1 mM, 100 $\mu$M, and 1 $\mu$M concentrations, respectively (FIG. 4). Even at 1 nM (i.e., $10^{-9}$ M) of 8-bromo cyclic GMP there was a 25% decrease in DNA synthesis in the adenocarcinoma cells (P<0.05) (FIG. 4). At 100 pM of 8-bromo cyclic GMP, its effects on DNA synthesis in these adenocarcinoma cells became not significant (14% decrease).

Prostaglandin $E_2$ Inhibits DNA Synthesis in Adenocarcinoma Cells

Figure 5:
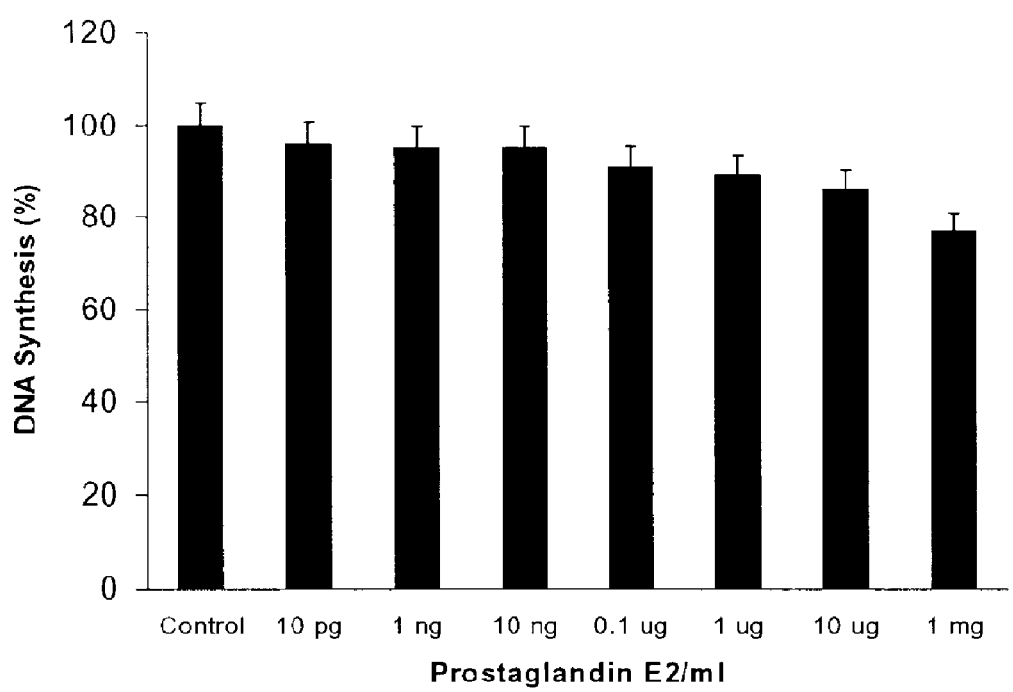
FIG. 5 is graph showing Prostaglandin $E_2$ (intracellular mediator of some of the peptides' effects) inhibits DNA synthesis in pancreatic adenocarcinoma cells. The decrease in DNA synthesis by prostaglandin $E_2$ at its 1 mg/ml concentration was significant at $P<0.05$ but the decrease in DNA synthesis at its 10 µg/ml, 1 µg/ml, 0.1 µg/ml, 10 ng/ml and 10 pg/ml concentrations did reach a level of significance when evaluated by repeated analysis of variance.

Part of the mechanism of action of long acting natriuretic peptide, vessel dilator and kaliuretic peptide's natriuretic effects involves enhancing the synthesis prostaglandin $E_2$ which, in turn, inhibits $Na^+$—$K^+$-ATPase in the kidney. Since prostaglandin $E_2$ mediates some of the effects of these peptide hormones, it was investigated whether prostaglandin $E_2$ may inhibit DNA synthesis in these cancer cells similar to cyclic GMP. Prostaglandin $E_2$ decreased DNA synthesis 23% (P<0.05) in these pancreatic adenocarcinoma cells at its 1 mg/ml concentration (FIG. 5). Dose-response curves revealed that prostaglandin $E_2$ decreased DNA synthesis in these adenocarcinoma cells 14%, 11%, 9%, 5%, 5%, and 4% (all non-significant) at its 10 $\mu$g/ml, 1 $\mu$g/ml, 0.1 $\mu$g/ml, 10 ng/ml, 1 ng/ml, and 10 pg/ml concentrations, respectively (FIG. 5).

LANP, Vessel Dilator, Kaliuretic Peptide and ANP's Effects on Apoptosis

To help determine whether these peptides were affecting apoptosis, these peptides' effects were examined within these adenocarcinoma cells on several of the caspases, a family of cysteine asparatic proteases which are central regulators of apoptosis. There was very little of baseline caspase activity (i.e., apoptosis) in these adenocarcinoma cells (FIG. 6). These four peptide hormones did not have any significant enhancement of caspases 9, 3, and 7 or of cleaved caspases 9, 3, and 7. They also had no significant effect on poly (ADP ribose) polymerase (PARP) or cleaved PARP (FIG. 6).

Vessel Dilator Inhibits the Growth of Human Pancreatic Adenocarcinomas In Vivo

To determine if any of the above peptide hormones can inhibit the growth of human adenocarcinomas in vivo, NCr athymic mice were injected subcutaneously with $1 \times 10^6$ human pancreatic adenocarcinomas cells. In approximately two weeks these cancer cells develop into a well-defined palpable cancer (approximately 1×1 mm; volume=0.5 mm$^3$). Human pancreatic adenocarcinoma was chosen for this investigation as it has the lowest 5-year survival of all common cancers (i.e., 1%). This cancer rapidly doubles in size approximately every two days. After 1 week the tumors in 14 control animals averaged 5×4 mm (volume=40 mm$^3$). For this in vivo investigation, vessel dilator was chosen to be investigated as it decreased the number of human adenocarcinoma cells the most in vitro. These tumors were allowed to consolidate a fairly large mass (8×5.5 mm; volume=121 mm$^3$, average) before the vessel dilator infusion was begun. Vessel dilator when infused for 14 days via a subcutaneous infusion pump at a concentration of 139 ng/min/kg of body weight stopped the growth of the human adenocarcinomas (and decreased their size slightly, n=14). At the same time in animals given a saline infusion, the adenocarcinomas continued to grow exponentially up to 20×20 mm (volume=4 cm$^3$) within 4 to 5 weeks. During the two weeks of vessel dilator infusion, the inhibition of growth of the adenocarcinomas (no increase in volume) was significant at (P<0.001) compared to the placebo (saline) treated adenocarcinomas (where volume increased 100 mm$^3$ during this same two-week time period). When the vessel dilator infusion ceased, the human adenocarcinomas began to grow (i.e., increase in size) again. Conclusion: This is the first evidence that one of these four peptide hormones (i.e., vessel dilator) can inhibit the growth of any cancer (e.g. human pancreatic adenocarcinoma) in vivo. There were no side effects with infusing this concentration of vessel dilator in whole animals.

This investigation is the first evidence that vessel dilator, LANP and kaliuretic peptide can decrease the number(s) of any cancer cell. ANP has been investigated once previously and reported to decrease the number of hepatoblastoma cells but the hepatoblastoma cells were not actually counted, rather the cell number was estimated based upon the formazan formation after a four-hour incubation with 3-(4,5-dimethylthiazol-2-yl)-2,5-diphenyl tetrazolium bromide). The present investigation in the first investigation of ANP and any cancer cells in which the number of cancer cells was directly counted. That all four peptide hormones decreased the number of pancreatic adenocarcinoma cells is especially noteworthy since adenocarcinoma of the pancreas is the most common lethal cancer with a mean survival of four months and a five-year survival of only 1%. Pancreatic adenocarcinomas are highly associated with cigarette (tobacco) smoking. The ability of these peptide hormones to decrease the number adenocarcinoma cells may have implication(s) for adenocarcinomas at other sites in the body with the majority of cancers of the breast, prostate and colon also being adenocarcinomas. Adenocarcinomas also occur in the lung where they have been highly associated with cigarette tobacco smoke (both smoking the cigarette itself and with "by-stander" cigarette smoke where the non-smoker is exposed to cigarette smoke in high concentration in a confined space). Adenocarcinomas of the lung have now become the most common type of lung cancer.

Vessel dilator was the most potent of these peptide hormones decreasing the number of adenocarcinoma cancer cells. Vessel dilator had significant (P<0.001) effects within 24 hours (65% decrease in number of cancer cells) and inhibited any further proliferation of the adenocarcinoma cells from 24 to 96 hours (P<0.001). This data suggests that vessel dilator has anticancer properties, decreasing the number of cancer cells and their proliferation. The 70% decrease in the number of cancer cells growing at 72 and 96 hours being markedly better than 5-Florouracil (5-FU), which was the standard chemotherapy for 45 years to treat pancreatic adenocarcinomas. For example, in one study 5-FU decreased the number of pancreatic adenocarcinomas in culture by 16%.

The other three cardiac peptides also decreased the number of the pancreatic adenocarcinoma cells more than 5-FU, with LANP being the next most potent with an approximate 50% decrease in the number of cancer cells. Each of these peptide hormones decreased the number of pancreatic adenocarcinoma cells at least 2-fold more than 5-FU-induced decrease in pancreatic adenocarcinoma cells. It should be noted that there was no decrease in the number of cells when examined immediately after addition of the respective peptide hormones indicating that the data obtained was not due to artifact. Further, it is important to note that cellular debrie was present at 24 hours in the peptide hormone-treated cell cultures suggesting that cellular necrosis of the cancer cells was occurring. It will be of interest in the future to add these four peptide hormones together in various combinations, and, especially of interest, to add the two most potent inhibitors vessel dilator and LANP together with these adenocarcinoma cells to determine if together they can decrease the number of these cancer cells even more than 70% of these cancer cells.

The mechanism of these peptide hormones' ability to decrease the number of adenocarcinoma cells was investigated to evaluate the hypothesis that the mechanism was due to their inhibiting DNA synthesis and/or enhancing the suicidal death of these adenocarcinoma cells. Each of these peptide hormones inhibited 83% or greater of the DNA synthesis in these adenocarcinoma cells. These findings suggest that the majority of the inhibition of growth of the pancreatic adenocarcinoma cells was via their ability to inhibit DNA synthesis. This finding is similar to ANP's ability to inhibit DNA synthesis in rat mesangial cells by 47% to 60% but considerably more significant than its ability to inhibit DNA synthesis in hepatoblastoma cells (22%). Vessel dilator, long acting natriuretic peptide, and kaliuretic peptide have never previously been investigated with respect to their ability to inhibit DNA synthesis.

With regard to the mechanism of how these peptide hormones inhibit DNA synthesis, one of the second messengers of their biologic effects, i.e., cyclic GMP was found using 8-bromo cyclic GMP to inhibit DNA synthesis up to 51% in these pancreatic adenocarcinoma cells. 8-bromo cyclic GMP mimicking the effects of these peptide hormones on DNA synthesis in the same cells suggests that cyclic GMP is one of the mediators of these peptide hormones' ability to inhibit DNA synthesis in adenocarcinoma cells. These findings are similar to cyclic GMP's previously reported antiproliferative (i.e., DNA synthesis inhibiting) effects in normal cells. Likewise, the other known mediator of some of these peptide hormones' biologic effects, i.e., prostaglandin $E_2$ also inhibited DNA synthesis but to a lesser extent (23%) than cyclic GMP. Because of the very high concentrations of $PGE_2$ needed to inhibit DNA synthesis in the pancreatic adenocarcinoma cells, $PGE_2$ may not be a relevant mediator of the ability of these peptide hormones to inhibit DNA synthesis in these cancer cells. The lack of significant effects on apoptosis further suggest that the majority of these peptide hormones' anticancer effects are via their ability to markedly inhibit DNA synthesis rather than via stimulation of "suicidal" cell death. ANP induces apoptosis in cardiac myocytes but not in fibroblasts or smooth muscle cells, suggesting that ANP induced apoptosis may be myocyte specific. Tissue specificity and altered metabolism in cancer cells may be the reason no apoptosis was observed in the pancreatic adenocarcinoma cells.

The application also contains the first evidence that any of these peptide hormones can inhibit any cancer growing within in a whole intact animal. The peptide hormone treatment was not begun until the human pancreatic adenocarcinoma was relatively large. It is important to note that the cancer utilized is the most lethal of all common cancers. This relatively large cancer was treated with a fairly low concentration of vessel dilator to be sure there would be no side effects of this treatment. There were no side effects of this treatment. One might anticipate that with large concentrations of these peptide hormones and/or when used together in combination with each other or with other anticancer agents that even a more marked inhibition/or sustained inhibition of cancer growth will occur. The ability of vessel dilator to inhibit the growth of adenocarcinomas growing in whole animals demonstrates the utility of this peptide hormone as an anti-cancer agent.

The present invention includes a method of utilizing four peptide hormones to inhibit the growth of cancer(s). A dramatic decrease in the number of human pancreatic adenocarcinoma cells (i.e., the type of cancer with the highest mortality, with patients only surviving four months) was observed responsive to treatment. Of these four peptide hormones, vessel dilator decreased the number of adenocarcinoma cells 65–70%, i.e., there were 65% less cancer cells present at 24 hours when exposed to vessel dilator and 70% less cancer cells present at 96 hours compared to the adenocarcinoma cells that were not treated with vessel dilator. The second of these peptide hormones, i.e., long acting natriuretic peptide, decreased the number of the human pancreatic adenocarcinoma cells by 47% at 24 hours and 48% at 96 hours. The third peptide hormone i.e., kaliuretic peptide decreased the number of adenocarcinoma cells by 37% (24 hours) and 42% (96 hours), respectively. Atrial natriuretic peptide, a fourth peptide hormone, decreased the number of pancreatic adenocarcinoma cells growth by 34% (24 hours) and 35% (96 hours). The mechanism of action of these peptide hormones' anticancer effects was found to be due to their ability to inhibit 83% or greater of the DNA synthesis within these adenocarcinoma cells (FIG. 3). The potential patent would be to utilize one or more of these peptide hormones alone and/or in combination to treat cancer. The ability of these peptide hormones to decrease the number of adenocarcinoma cells may have implication(s) for the same cancer cell type, i.e. adenocarcinomas at other sites in the body with the majority of cancers of the breast, colon and prostate also being adenocarcinomas. Adenocarcinomas also occur in the lung and other tissues. Treatment of a wide variety of cancers in addition to adenocarcinomas is anticipated by the present invention.

Figure 7:
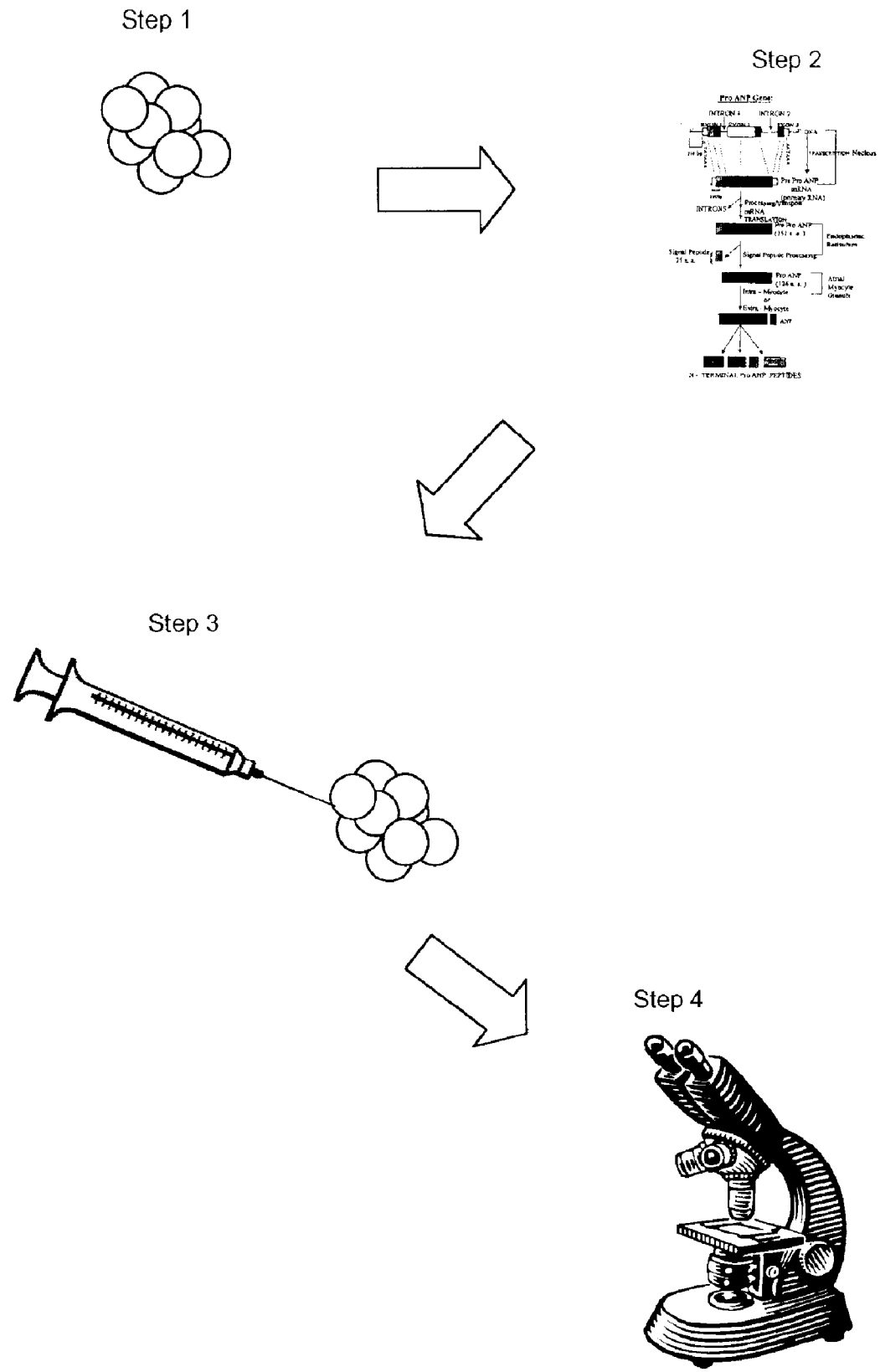
FIG. 7 is a graphic representation of the inventive method.

In summary, FIG. 7, illustrates the inventive method. In step 1 adenocarcinoma cells are identified, either in vivo or in vitro. In step 2 the proper peptide hormone (or combination of peptide hormones or as an adjunct to other chemotherapeutic agents), derived from the ANP prohormone, is selected and given to the patient. The target adenocarcinoma cells are then contacted with an effective amount (discussed infra) of the peptide hormone(s) in step 3. Finally, in step 4, the remaining adenocarcinoma cells are quantified and the patient is evaluated for the need for further treatment.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pennsylvania, Mack Publishing Company, 19$^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The administration of theprohormone compounds are administered and dosed in accordance with good medical practice, taking into account the clinical condition of the individual patient, the site and method of administration, scheduling of administration, patient age, sex, body weight, and other factors known to medical practitioners.

The pharmaceutically "effective amount" for purposes herein is thus determined by such considerations as are known in the art.

A therapeutically effective amount of each respective peptide hormone, or any combination thereof, is that amount necessary to provide a therapeutically effective amount of the corresponding procyanidin in vivo. The amount of prohormone must be effective to achieve a response. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of inhibiting the growth of cancer cells comprising the step of contacting at least one target cell with an effective amount of a peptide hormone derived from the atrial natriuretic peptide prohormone.

2. The method of claim 1 where the peptide hormone derived from the atrial natriuretic peptide prohormone is selected from the group consisting of atrial natriuretic peptide, long acting natriuretic peptide, vessel dilator, and kiliuretic peptide.

3. The method of claim 1 wherein the target cell is either an adenocarcinoma, small cell or squamous cell carcinoma.

4. The method of claim 1 wherein the effective amount of peptide hormone is administered to at least one target cell.

5. A method of inhibiting the growth of cancer cells comprising the step of co-administering, to at least one target cell, an effective amount of a combination of peptide hormones derived from the atrial natriuretic peptide prohormone.

6. The method of claim 5 where the combination of peptide hormones derived from the atrial natriuretic peptide prohormone is selected from the group consisting of atrial natriuretic peptide, long acting natriuretic peptide, vessel dilator, and kiliuretic peptide.

7. The method of claim 5 wherein the target cell is an adenocarcinoma, small cell or squamous cell carcinoma.

8. The method of claim 5 wherein the effective amount of the combination of peptide hormones is administered to at least one target cell.

9. A method of inhibiting the growth of cancer cells comprising the step of contacting at least one target cell with an effective amount of a peptide hormone derived from the atrial natriuretic peptide prohormone, wherein the peptide hormone derived from the atrial natriuretic peptide prohormone is selected from the group consisting of atrial natriuretic peptide, long acting natriuretic peptide, vessel dilator, and kiliuretic peptide, where the target cell is chosen from the group consisting of adenocarcinoma, small cell and squamous cell carcinoma, and the effective amount of peptide hormone is administered to at least one target cell.

10. A method of inhibiting the growth of cancer cells comprising the step of co-administering, to at least one target cell, an effective amount of a combination of peptide hormones derived from the atrial natriuretic peptide hormone, wherein the combination of peptide hormones derived from the atrial natriuretic peptide prohormone is selected from the group consisting of atrial natriuretic peptide, long acting natriuretic peptide, vessel dilator, and kiliuretic peptide, where the target cell is chosen from the group consisting of adenocarcinoma, small cell and squamous cell carcinoma, and the effective amount of the combination of peptide hormones is administered to at least one target cell.

* * * * *